US008435950B2

(12) United States Patent
Dal Farra et al.

(10) Patent No.: US 8,435,950 B2
(45) Date of Patent: May 7, 2013

(54) ANTI-AGING PEPTIDES AND COSMETIC AND/OR PHARMACEUTICAL COMPOSITION CONTAINING SAME

(75) Inventors: Claude Dal Farra, Kerhonkson, NY (US); Nouha Domloge, Valbonne (FR); Jean-Marie Botto, Valbonne (FR); Isabelle Imbert, Paris (FR)

(73) Assignee: ISP Investments, Wilmington, DE (US)

( * ) Notice: Subject to any disclaimer, the term of this patent is extended or adjusted under 35 U.S.C. 154(b) by 0 days.

(21) Appl. No.: 13/143,741

(22) PCT Filed: Jan. 7, 2010

(86) PCT No.: PCT/FR2010/000007
§ 371 (c)(1),
(2), (4) Date: Jul. 8, 2011

(87) PCT Pub. No.: WO2010/079285
PCT Pub. Date: Jul. 15, 2010

(65) Prior Publication Data
US 2011/0269694 A1  Nov. 3, 2011

(30) Foreign Application Priority Data
Jan. 9, 2009  (FR) ..................... 09 00069

(51) Int. Cl.
*A61K 38/08* (2006.01)
*A61K 38/07* (2006.01)
*A61Q 19/08* (2006.01)
*C07K 5/00* (2006.01)

(52) U.S. Cl.
USPC ....... 514/18.8; 514/18.6; 514/21.7; 514/21.8; 514/21.9; 530/328; 530/329; 530/330

(58) Field of Classification Search .................. None
See application file for complete search history.

(56) References Cited

U.S. PATENT DOCUMENTS

| 6,291,429 | B1 | 9/2001 | Takahaski et al. |
| 2005/0271650 | A1* | 12/2005 | Freimark et al. ........... 424/130.1 |
| 2008/0039403 | A1* | 2/2008 | Andersen et al. ............... 514/16 |
| 2009/0292111 | A1 | 11/2009 | Yamamoto et al. |

FOREIGN PATENT DOCUMENTS

| EP | 1864997 | 12/2007 |
| WO | 93/11231 | 6/1993 |
| WO | 99/57137 | 11/1999 |
| WO | WO 2007/071248 A2 * | 6/2007 |

OTHER PUBLICATIONS

Merck Manual Home Edition. Effects of Aging on the Skin. Oct. 2006, p. 1.*
Chronic Effects of Sunlight, from Merck Manual, Aug. 2007, pp. 1-2.*
PCT, International Search Report, International Application No. PCT/FR2010/000007 (mailed Jun. 7, 2010, published Jul. 15, 2010).
PCT, International Preliminary Report on Patentability, International Application No. PCT/FR2010/000007 (Aug. 2, 2011).
Ando, S. et al., "Phosphorylatino of Synthetic Vimentin Peptides by CDC2 Kinase" *Biochemical and Biophysical Research Communications*, vol. 195, No. 2, pp. 837-843 (Jan. 15, 1993).
Hirayama, J. et al., "Structural and functional features of transcription factors controlling the circadian clock," *Current Opinion in Genetics & Development*, vol. 15, No. 5, pp. 548-556 (Oct. 2005).
Kondratov, R.V, "A role of the circadian system and circadian proteins in aging," *Ageing Research Reviews*, vol. 6, No. 1, pp. 12-27 (May 2007).
Kullmann, W., "Proteases as Catalysts for Enzymic Syntheses of Opioid Peptides," The Journal of Biological Chemistry, vol. 255, No. 17, pp. 8234-8238 (Sep. 10, 1980).
Tanioka, M. et al., "Molecular Clocks in Mouse Skin," *Journal of Investigative Dermatology*, vol. 129, No. 5, pp. 1225-1231 (Nov. 27, 2008).
Weinert, D., "Age-Dependent Changes of the Circadian System," *Chronobiology International*, 17(3), pp. 261-283 (2000).

* cited by examiner

*Primary Examiner* — Julie Ha
*Assistant Examiner* — Li Ni Komatsu
(74) *Attorney, Agent, or Firm* — Thompson Hine L.L.P.

(57) ABSTRACT

The present invention relates to peptide compounds of general formula (I)

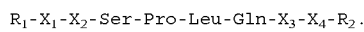

$R_1-X_1-X_2-Ser-Pro-Leu-Gln-X_3-X_4-R_2$.

The present invention also relates, on the one hand, to a cosmetic or pharmaceutical composition comprising at least one peptide of general formula (I) in a cosmetically or dermatologically acceptable medium, and on the other hand to its use in order to prevent or treat the cutaneous signs of aging and to protect the skin against the harmful effects caused by UV radiation.
The invention lastly relates to a cosmetic treatment method for preventing and/or combatting cutaneous signs of aging and for protecting the skin against the harmful effects caused by UV radiation.

14 Claims, No Drawings

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 1

Ser Pro Leu Gln
1

<210> SEQ ID NO 2
<211> LENGTH: 5
<212> TYPE: PRT
<213> ORGANISM: Artificial
<220> FEATURE:
```

-continued

```
<223> OTHER INFORMATION: Synthetic peptide

<400> SEQUENCE: 2

Thr Ser Pro Leu Gln
1               5

<210> SEQ ID NO 3
<211> LENGTH: 6
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 3

Ser Ser Pro Leu Gln Leu
1               5

<210> SEQ ID NO 4
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: AMIDATION

<400> SEQUENCE: 4

Ser Ser Pro Leu Gln Ala Asn
1               5
```

ANTI-AGING PEPTIDES AND COSMETIC AND/OR PHARMACEUTICAL COMPOSITION CONTAINING SAME

The present invention relates to peptide compounds of general formula $R_1$-$X_1$-$X_2$-Ser-Pro-Leu-Gln-$X_3$-$X_4$-$R_2$ and to their uses in cosmetics and/or pharmaceuticals in order to prevent and correct the effects of aging and the harmful effects of UV radiation on the skin and skin appendages.

The first function of the epidermis is to form a barrier between the external environment and the internal medium. It is the outermost layer of the epidermis, the stratum corneum, which carries out this task. It is formed of keratinocytes at the final stage of their differentiation: corneocytes, which are cemented to one another by a thick intercellular cement which is both flexible and impermeable. This physical barrier which is the skin makes it possible for the human body to protect itself against numerous types of attack. These attacks can have different intrinsic origins, such as chronological aging or else biochemical changes which take place during states of fatigue, stress or hormonal changes such as those during pregnancy, etc. Other attacks are extrinsic in origin, such as pollution, the sun, disease, etc. In response to these attacks, the appearance of the skin is changed and the appearance of wrinkles and fine lines, areas of hyper- or hypopigmentation, dryness or even dehydration of the skin, a thinning of the epidermis, elastosis, imperfections, aged areas, etc. is observed. These changes are caused by the alteration to the functions of cellular renewal, cellular cohesion and synthesis of collagen, elastin and other proteins, and ultimately lead to a decrease in the protective barrier qualities of the skin and to a less attractive appearance thereof. All these changes affect not only the skin, but also the skin appendages such as the nails and hair. For example, hair becomes lifeless or greying, or else falls out prematurely.

Numerous cosmetic compositions have been proposed in recent years in order to overcome these drawbacks. These compositions included the use, either alone or in combination, of hydrating, soothing, anti-inflammatory, free anti-radical, antiseborrheic, healing, brightening and keratolytic agents, etc. However, none of these compositions currently makes it possible to prevent or correct the signs of aging, of intrinsic or extrinsic origin, of the skin.

Surprisingly, the applicant has discovered that peptide compounds of the following general formula $R_1$-$X_1$-$X_2$-Ser-Pro-Leu-Gln-$X_3$-$X_4$-$R_2$ had an anti-aging effect on the skin as a result of a global action on various characteristic symptoms thereof. No. document of the prior art describes such peptide compounds in order to obtain an anti-aging effect. Furthermore, these peptide compounds are characterized by the fact that they are activator agents of the Clock gene involved in the regulation of the circadian cycle. Consequently, the present invention relates to peptide compounds which are Clock (circadian locomotor output cycles kaput) activators and to their use in cosmetic and pharmaceutical compositions in order to prevent or correct the signs caused by aging and the harmful effects of UV radiation on the skin and skin appendages.

The circadian clock is controlled by a negative regulation loop involving a set of genes, in particular the Per-1 (period), Clock and BMAL-1 (brain and muscle ARNt-like protein) genes.

It has been demonstrated that aging is accompanied by a change in the biological rhythms, with a decrease in amplitude and a tendency towards phase lead (Weinert D., Chronobiol. Int. 2000; 17:261-83). Furthermore, it has been shown that the circadian clock was altered by this same aging process.

Previously, in the prior art, numerous applications have already been proposed with regard to the use of nucleotides and/or proteins produced by Clock, Per-1 or BMAL-1 genes. For example, see U.S. Pat. No. 6,291,429 which describes the use of the product of the Clock gene to resynchronise the sleep cycle or physiological or endocrinal processes, or to resynchronize the body after jet lag, etc. However, no. document of the prior art describes the use of specific Clock activator peptides in order to prevent or correct the signs of aging or else the consequences of the harmful effects of UV radiation.

The present invention firstly relates to a peptide compound of formula (I) below:

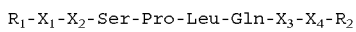
$$R_1\text{-}X_1\text{-}X_2\text{-Ser-Pro-Leu-Gln-}X_3\text{-}X_4\text{-}R_2$$

in which
$X_1$ is a cysteine, a methionine or is equal to zero,
$X_2$ is a serine, a threonine, or is equal to zero,
$X_3$ is an alanine, a glycine, an isoleucine, a leucine, a proline, a valine or is equal to zero,
$X_4$ is an asparagine, a glutamine, or is equal to zero,
$R_1$ is the primary amine function of the N-terminal amino acid, either free or substituted by a protective group which can be selected from an acetyl group, a benzoyl group, a tosyl group or a benzyloxycarbonyl group,
$R_2$ is the hydroxyl group of the carboxyl function of the C-terminal amino acid, either free or substituted by a protective group which can be selected from a $C_1$ to $C_{20}$ alkyl chain or a $NH_2$, NHY or NYY group where Y is a $C_1$ to $C_4$ alkyl chain,
said sequence of general formula (I) being formed of 4 to 8 amino acid residues,
said sequence of general formula (I) possibly comprising substitutions of amino acids $X_1$ to $X_4$ with other chemically equivalent amino acids.

The present invention secondly relates to a cosmetic or dermopharmaceutical composition comprising peptide compounds of general formula (I).

The present invention thirdly relates to the use of a cosmetic or dermopharmaceutical composition comprising peptide compounds of general formula (I).

Lastly, the present invention fourthly relates to a cosmetic treatment method carried out with the aid of a composition comprising a peptide compound of general formula (I).

The first object of the invention relates to a peptide compound of general formula (I) below:

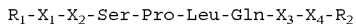
$$R_1\text{-}X_1\text{-}X_2\text{-Ser-Pro-Leu-Gln-}X_3\text{-}X_4\text{-}R_2$$

in which
$X_1$ is a cysteine, a methionine or is equal to zero,
$X_2$ is a serine, a threonine, or is equal to zero,
$X_3$ is an alanine, a glycine, an isoleucine, a leucine, a proline, a valine or is equal to zero,
$X_4$ is an asparagine, a glutamine, or is equal to zero,
$R_1$ is the primary amine function of the N-terminal amino acid, either free or substituted by a protective group which can be selected from an acetyl group, a benzoyl group, a tosyl group or a benzyloxycarbonyl group,
$R_2$ is the hydroxyl group of the carboxyl function of the C-terminal amino acid, either free or substituted by a protective group which can be selected from a $C_1$ to $C_{20}$ alkyl chain or a $NH_2$, NHY or NYY group where Y is a $C_1$ to $C_4$ alkyl chain, said sequence of general formula (I) being formed of 4 to 8 amino acid residues,
said sequence of general formula (I) possibly comprising substitutions of amino acids $X_2$ to $X_4$ with other chemically equivalent amino acids.

In order to improve the resistance to degradation, it may be necessary to use a protected form of the peptide according to the invention. The form of protection must, of course, be a biologically compatible form and must be compatible with a use within the field of cosmetics or pharmacy. The peptide compound preferably has at least one functional group protected by a protective group, said protective group being an acetylation of the amino-terminal end or an amidation or esterification of the carboxy-terminal end, or both. A protection based on amidation of the hydroxyl function of the carboxyl-terminal end with a NYY group in which Y is a $C_1$ to $C_4$ alkyl chain, or esterification with an alkyl group is preferably used.

The peptide compound preferably has one of the following sequences:

```
(SEQ ID no. 1)    Ser-Pro-Leu-Gln-NH₂

(SEQ ID no. 2)    Thr-Ser-Pro-Leu-Gln (SEQ ID no. 3)    Ser-Ser-Pro-Leu-Gln-Leu-NH₂

(SEQ ID no. 4)    Ser-Ser-Pro-Leu-Gln-Ala-Asn-NH₂
```

In a specific embodiment the sequence of the peptide compound is the sequence SEQ ID no.1, i.e. Ser-Pro-Leu-Gln-NH$_2$.

The invention also relates to homologous forms of these sequences. The term "homologous" means, in accordance with the invention, any peptide sequence which is identical to at least 50%, or preferably at least 80%, and even more preferably at least 90% of said peptide sequence, selected from the sequences SEQ ID no.1 to SEQ ID no.4. "Peptide sequence identical to at least X %" is understood to denote a percentage of identity between the amino.acid residues of the two sequences to be compared, obtained after optimal alignment of the two sequences. Optimal alignment is obtained with the aid of algorithms of local homologies, such as those used by the IT software BLAST P or T BLAST N available on the NCBI site.

The term "homologous" can also denote a peptide which differs from the sequence of a peptide of sequence SEQ ID no.1 to SEQ ID no.4 by the substitution of chemically equivalent amino.acids, i.e. by the substitution of one residue with another having the same characteristics. Thus, conventional substitutions are made between Ala, Val, Leu and Ile; between Ser and Thr; between the acid residues Asp and Glu; between Asn and Gln; and between the basic residues Lys and Arg; or between the aromatic residues Phe and Tyr.

The term "peptide" denotes a sequence of two or more amino.acids linked together by peptide bonds or by modified peptide bonds.

"Peptide" must be understood to mean the natural or synthetic peptide of the invention as described above, or at least one of its fragments, whether obtained by proteolysis or synthetically, or else any natural or synthetic peptide, the sequence of which is formed in whole or in part by the sequence of the peptide described above.

The peptide of general formula (I) according to the invention can be obtained either by conventional chemical synthesis (in solid phase or in homogeneous liquid phase), or by enzymatic synthesis (Kullman et al., J. Biol. Chem. 1980, 225, 8234), from constitutive amino.acids or derivatives thereof.

The peptide according to the invention can be of natural or synthetic origin. In accordance with the invention the peptide is preferably obtained by chemical synthesis.

Lastly, the active ingredient can be a single peptide, a mixture of peptides or of peptide derivatives and/or derivatives formed of amino.acid derivatives.

The peptide compound according to the invention can be used as a medicament.

The second object of the present invention relates to cosmetic compositions comprising said peptide compound of general formula (I). The compositions according to the invention are preferably present in a form adapted for topical application comprising a cosmetically or dermatologically acceptable medium. "Cosmetically or dermatologically acceptable" means media which are suitable for a use in which they come into contact with the skin or human skin appendages without posing a risk of toxicity, intolerance, instability, allergic reaction, etc. Said peptide compound is preferably present in the composition at a concentration between approximately 0.0005 and 500 ppm, and preferably at a concentration between 0.01 and 5 ppm. In the compositions according to the invention, the peptide compound is previously solubilized in one or more cosmetically or dermatologically acceptable solvents, such as water, glycerol, ethanol, propylene glycol, butylene glycol, dipropylene glycol, ethoxylated or propoxylated diglycols, cyclic polyols, petroleum jelly, a vegetable oil or any mixture of these solvents.

In accordance with yet a further advantageous embodiment the active ingredient according to the invention is previously solubilized in a cosmetic or pharmaceutical vector such as liposomes, or adsorbed on pulverulent organic polymers, mineral supports such as talcs and bentonites, and more generally solubilized in, or fixed on, any physiologically acceptable vector.

The compositions to be applied to the skin can be present in the form of aqueous or hydroalcoholic solution, an oil-in-water or water-in-oil emulsion, a microemulsion, aqueous or anhydrous gels, serum, or else a dispersion of vesicles, a patch, cream, spray, salve, ointment, lotions, gel, solution, suspension, etc. The compositions can also be applied to the skin appendages in the form of a shampoo, dye or mascara to be applied by a brush or a comb, in particular to the eyelashes, eyebrows or hair, or else in the form of nail care, such as varnishes.

In a specific embodiment the composition according to the invention also contains at least one further active ingredient which promotes the action of said peptide active ingredient. Non-limiting examples include the following classes of ingredients: other peptide active ingredients, vegetable extracts, healing agents, anti-age agents, anti-wrinkle agents, soothing agents, anti-radical agents, anti-UV agents, agents stimulating the synthesis of dermal macromolecules or the energy metabolism, hydrating agents, anti-bacterial agents, anti-fungal agents, anti-inflammatory agents, anaesthetic agents, agents modulating cutaneous differentiation, pigmentation or depigmentation, agents stimulating nail or hair growth, etc. An anti-radical or anti-oxidant agent or an agent stimulating the synthesis of dermal macromolecules, or else an agent stimulating the energy metabolism is preferably used.

Furthermore, additives such as thickening, emulsifying, humectant and emollient agents, perfumes, anti-oxidants, filmogenic agents, chelating agents, sequestering agents, conditioning agents, etc. can be added to the composition.

In any case, the person skilled in the art will ensure that these additives as well as the amounts thereof are selected so as not to be detrimental to the desired, advantageous properties of the composition according to the invention. For example, these additives may correspond to 0.01 to 20% of the total weight of the composition. When the composition of the invention is an emulsion, the fatty phase can be from 5 to 80% by weight, and preferably from 5 to 50% by weight based on the total weight of the composition. The emulsifiers and co-emulsifiers used in the composition will be selected from those conventionally used in the field concerned. For example, they can be used in a proportion of from 0.3 to 30% by weight, based on the total weight of the composition.

A third object of the present invention relates to the use of the peptide compound as defined above as a Clock activator active ingredient. A "Clock activator" peptide compound means any peptide or derivative which is biologically capable of increasing Clock activity, either by increasing Clock protein synthesis (by direct or indirect modulation of Clock gene expression) or by other biological processes such as stabilization of Clock protein or else stabilization of the RNA messenger transcripts.

A fourth object of the present invention relates to the use of a composition comprising said peptide compound in order to prevent or treat the cutaneous signs of aging. The "cutaneous signs of aging" include, but are not limited to, any visible manifestations on the skin caused by aging. In particular, this means wrinkles, fine lines, chapped skin, enlarged pores, imperfections, losses in firmness, discoloration, aged areas, keratosis, losses in collagen, and other changes to the dermis and epidermis, etc. "Cutaneous signs of aging" also means any changes to the outer appearance of the skin and skin appendages caused by aging, such as superficial roughness of the corneal layer, but also any internal change to the skin which is not translated systematically into a modified outer appearance, such as thinning of the dermis or any other internal degradation of the skin.

Furthermore, the present invention relates to the use of a composition according to the invention for protecting the skin against the harmful effects caused by UV radiation.

A further object of the invention relates to the use of an effective amount of peptide active ingredient according to the invention to prepare a pharmaceutical composition for preventing or combating the pathologies associated with oxidation processes.

A final object of the present invention relates to a cosmetic treatment method, characterized in that a composition containing an effective amount of peptide active ingredient is applied topically to the skin or skin appendages in order to prevent or treat the cutaneous signs of aging or to protect the skin against the harmful effects caused by UV radiation. Furthermore, this cosmetic treatment method is characterized in that the composition is applied before going to sleep so as to respect the circadian rhythm of the skin in order to have a rejuvenating effect on the skin. In fact, during the night, the skin promotes renewal functions as well as metabolic synthesis processes. Consequently, by respecting the biological rhythm of the skin, the application of the composition as claimed makes it possible to obtain a rejuvenating effect, which stimulates cellular renewal, and a regenerative effect.

The examples below describe and demonstrate the efficacy of peptide compounds as described according to the invention. The cosmetic formulation mentioned is representative of the invention but is given merely by way of example and should not be interpreted as a limitation of the present invention.

EXAMPLE 1

Demonstration of the Activating Effect of the Peptide SEQ ID No.1 on the Expression of the Clock Protein in Cultured Fibroblasts A study of the activating effect of the peptide SEQ ID no.1 was carried out by evaluating the expression of the Clock protein by western blot in cultured fibroblasts and by immunohistochemistry by labeling the Clock protein by means of immunolabeling. The technique of western blotting is a semi-quantitative method which makes it possible to evaluate the level of Clock protein in dermal cells.

Protocol a) Study by Western Blot

Cultured fibroblasts are cultivated in containers with a diameter of 100 mm at 37° C. in a humidified atmosphere containing 5% $CO_2$ for 16 hr in the presence or absence of the peptide SEQ ID no.1, diluted to 1% (from a $10^{-4}$M solution). The cells are rinsed and then removed from the support with the aid of an extraction buffer (20 mM TRIS, 150 mM NaCl, 10 mM EDTA, 0.2% triton X10) in the presence of a cocktail of protease inhibitors (Sigma). The proteins thus extracted are centrifuged at 4° C. at 10000 rpm, before being dosed by the BCA protein dosing kit (Pierce). The cellular lysates are mixed with a denaturing buffer and subjected to SDS-PAGE electrophoresis. The gel used is 4-12% Nupage (Invitrogen). The proteins are then transferred to a nitrocellulose membrane (Pal corporation). The membranes are saturated in 5% PBS-milk and 0.1% tween 20 for 2 hours at ambient temperature, then incubated at 4° C. overnight with an anti-clock primary antibody (ABcam) diluted 1/1000 followed by incubation with an anti-rabbit secondary antibody Iggy-peroxidase diluted 1/5000. Viewing was carried out by a chemiluminescent substrate. The quantitative evaluation of the proteins present in the cells was carried out using the chemi-imager software (Alpha innotech Corporation USA). The amount of proteins is expressed as a percentage of the luminous intensity compared to the controlled condition which did not receive the treatment.

b) Study by Immunohistochemistry

Cultured fibroblasts are cultivated in 8-well chambers (labteck) at 37° C. in a humidified atmosphere containing 5% $CO_2$ for 18 hr in the presence or absence of the peptide SEQ ID no.1, diluted 1% (from a $10^{-4}$M solution). Untreated cells are cultivated at the same time and serve as a control. On the day of labeling the cells are rinsed, fixed in a mixture (2% glutaraldehyde—2% formaldehyde) for 3 minutes and then rinsed. The primary antibody (ABcam), diluted 1/250 is applied for 1 hour and a secondary antibody, diluted 1/50 and coupled to a fluorochrome is applied for 1 hour. The cells are then mounted between a slide and cover glass in a suitable mounting medium and observed under epifluorescence microscope.

Results:

The results obtained by western blot show that the treatment by peptide SEQ ID no.1, diluted 1% increases the amount of Clock protein present in the cultured fibroblasts. The results are summarised in the table below.

| Intensity (%) | Experiment 1 |
| --- | --- |
| Untreated control | 100% |
| 1% treatment | 179% |

These results are confirmed by the labeling of the Clock protein in the fibroblasts. In fact, an increase in the expression of the Clock protein is demonstrated in the treated fibroblasts.

Conclusion:

The administration of the peptide SEQ ID no.1 makes it possible to increase the amount of Clock protein in cultured dermal cells.

EXAMPLE 2

Demonstration of the Activating Effect of the Peptide SEQ ID No.1 on the Expression of the Clock and Per Proteins in Skin Biopsies A study of the activating effect of the peptide SEQ ID no.1 was carried out by evaluating the expression of Clock and Per-1 proteins in skin biopsies ex vivo.

Protocol

Ex vivo studies by immunolabeling have made it possible to evidence the expression of Clock and Per-1 proteins in skin samples. Samples of human skin are cultured at the air/liquid interface. The peptide SEQ ID no.1 diluted to 1% (from a $10^{-4}$M solution) is applied topically to these samples for 48 hr at a rate of two times per 24 hr.

Skin samples not treated with the peptide SEQ ID no.1 serve as a control. The skin samples are fixed with 10% formaldehyde and enclosed in paraffin. Sectional cuts of 3 μm are then made with a microtome. The immunolabeling is carried out after removal of the paraffin and unmasking of the antigenic sites.

The immunolabeling for the Clock protein is carried out by means of an antibody (ABcam) diluted 1/250 and a secondary antibody diluted 1/50 and coupled to a fluorochrome.

The immunolabeling for the Per-1 protein is carried out by a polyclonal antibody (Cosmobio) diluted 1/100 and a secondary antibody diluted 1/50 and coupled to a fluorochrome.

The slides are then mounted in a suitable medium and observed under epifluorescence microscope (Nikon Eclipse E600).

Results:

The results obtained show that the skin treated with the peptide SEQ ID no.1 express an amount of Clock protein which is slightly greater than that of the untreated skin. It is likewise demonstrated that the skin treated with the peptide SEQ ID no.1 express an amount of Per-1 protein which is greater than that of the untreated skin.

The semi-quantitative evaluation of the labeling is carried out by microscopic observation and is summarised in the table below.

|  | Untreated | Treated with peptide SEQ ID no. 1 diluted to 1% |
|---|---|---|
| Clock protein labeling | +/− | ++ |
| PER-1 protein labeling | + | + |

Conclusion:

The peptide SEQ ID no.1 makes it possible to increase the amount of Clock and PER-1 proteins in skin biopsies.

EXAMPLE 3

Demonstration of the Activating Effect of the Peptide SEQ ID No.1 on the Expression of Clock and Per-1 Proteins in Skin Biopsies During Aging A study of the activating effect of the peptide SEQ ID no.1 was carried out by evaluating the expression of Clock and Per-1 proteins in skin models, aged artificially during culture. The analysis was carried out after 62 hr and 134 hr of culturing.

Protocol

Ex vivo studies by immunolabeling have made it possible to evidence the expression of Clock and Per-1 proteins in skin samples aged during culture. Samples of human skin are cultured at the air/liquid interface for 62 hr and 134 hr. The peptide SEQ ID no.1 diluted to 1% (from a $10^{-4}$M solution) is applied topically to these samples at a rate of two times per day during the period of the experiment.

Skin samples not treated with the peptide SEQ ID no.1 serve as a control. The skin samples are fixed with 10% formaldehyde and enclosed in paraffin. Sectional cuts of 3 μm are made with a microtome. The immunolabeling is carried out after removal of the paraffin and unmasking of the antigenic sites. The immunolabeling for the Clock protein is carried out by means of an antibody (ABcam) diluted 1/250 and a secondary antibody diluted 1/50 and coupled to a fluorochrome.

The immunolabeling for the Per-1 protein is carried out by a polyclonal antibody (Cosmobio) diluted 1/100 and a secondary antibody diluted 1/50 and coupled to a fluorochrome.

The slides are then mounted in a suitable medium and observed under epifluorescence microscope (Nikon Eclipse E600).

Results:

The results obtained show that the labeling of the Clock protein (essentially epidermal) is increased after 62 hr of culturing compared to untreated control slides. Likewise, the expression of the PER-1 protein is increased after 62 hr of treatment. This labeling continues over time since after 134 hr the labeling of the Clock protein is largely increased compared to the untreated control skin. The table below gives a visual evaluation of the labeling.

|  |  | Untreated | Treated with peptide SEQ ID no. 1 diluted to 1% |
|---|---|---|---|
| Clock labeling | 62 h | + | ++ |
|  | 134 h | + | ++ |
| PER-1 labeling | 62 h | +/− | ++ |
|  | 134 h | +/− | + |

Conclusion:

The peptide SEQ ID no.1 makes it possible to increase the amount of Clock and PER-1 proteins in treated skin biopsies aged artificially during culture.

EXAMPLE 4

Demonstration of the Protective Effect of the Peptide SEQ ID No.1 on Skin Biopsies During Aging A study of the protective effect of the peptide SEQ ID no.1 was carried out in parallel by evaluating the damage caused by aging at 62 hr and 134 hr by way of immunohistology by means of colouration of sectional cuts of skin.

Protocol

Samples of human skin are placed in culture at the air/liquid interface. The peptide SEQ ID no.1 diluted to 1% (from a $10^{-4}$M solution) is applied topically to these samples for 62 hr and 134 hr. The application is renewed twice per day during the period of the experiment. Untreated skin samples serve as a control during the experiment. The skin samples are fixed with 4% formaldehyde and enclosed in paraffin. Sectional cuts of 3 μm are made with a microtome. The tissues are coloured using hematoxyline (which colours the cell nuclei blue-black) and eosin, which is specific to the colouration of cytoplasms. The morphological structure of the biopsies is then assessed under transmission microscope.

Results:

The results obtained show that the skin not treated with peptide SEQ ID no.1 is damaged, the cells are vacuolated, the cells appear damaged with cells of which the nuclei are very condensed (apoptotic signs). By contrast, the skin treated with peptide SEQ ID no.1 has a well-preserved morphological structure and the damage caused by aging is less visible. For the two experiments of 62 and 134 h, the peptide SEQ ID no.1 protects the biopsies of aging skin.

Conclusion:

The peptide SEQ ID no.1 makes it possible to evidence a protective effect on the structural morphology of skin biopsies subjected to artificial aging during culture.

EXAMPLE 7

Preparation of a Composition

Sun Protection Cream

| Brand names | INCI names | % by weight |
|---|---|---|
| PHASE A | | |
| Demineralised water | Aqua (water) | qsp |
| Pemulen TR1 | Acrylates/C10-30 alkyl Acrylate Crosspolymer | 0.40 |
| Glycerine | Glycerin | 3.00 |
| Nipastat Sodium | Sodium Methylparaben (and) Sodium Ethylparaben (and) Sodium Butylparaben (and) Sodium Propylparaben (and) Sodium Isobutylparaben | 0.15 |
| PHASE B | | |
| Parsol MCX | Ethylhexyl Methoxycinnamate | 7.50 |
| Eusolex 4360 | Benzophenone-3 | 3.00 |
| Parsol 1789 | Butyl Methoxydibenzoylmethane | 2.00 |
| Myritol 318 | Caprylic/Capric Triglyceride | 4.00 |
| Emulgade SEV | Hydrogenated Palm Glycerides (and) Ceteareth-20 (and) Ceteareth-12 (and) Cetearyl Alcohol | 5.00 |
| Propylparaben | Propylparaben | 0.15 |
| Nacol 16-98 | Cetyl Alcohol | 1.00 |
| PHASE C | | |
| TEA | Triethanolamine | 0.20 |
| PHASE D | | |
| Peptide SEQ ID no. 2 | | 3 ppm |
| Parfum | Parfum (Fragrance) | qsp |
| Colourant | | qsp |

The constituents of phase A and phase B are heated separately between 70° C. and 75° C. Phase B is emulsified in phase A with stirring. Phase C is added, at 45° C., increasing stirring. Phase D is then added when the temperature is below 40° C. Cooling is carried out to 25° C. with rapid stirring.

Applicants incorporate by reference the material contained in the accompanying computer readable Sequence Listing entitled "BV_US$_{13}$ 09_117_ST25.txt", which was created on Jun. 27, 2011, and is 1,084 bytes in size, and hereby confirm that the information recorded in the computer readable form is identical to the written sequence listing.

The invention claimed is:

1. A peptide compound of general formula (I) below:

$$R_1-X_1-X_2-Ser-Pro-Leu-Gln-X_3-X_4-R_2$$

wherein $X_1$ is a cysteine, a methionine or is equal to zero, $X_2$ is a serine, a threonine, or is equal to zero, $X_3$ is an alanine, a glycine, an isoleucine, a leucine, a proline, a valine or is equal to zero, $X_4$ is an asparagine, a glutamine, or is equal to zero, $R_1$ is the primary amine function of the N-terminal amino acid, either free or substituted by a protective group which can be selected from an acetyl group, a benzoyl group, a tosyl group or a benzyloxycarbonyl group, $R_2$ is the hydroxyl group of the carboxyl function of the C-terminal amino acid, either free or substituted by a protective group which can be selected from a $C_1$ to $C_{20}$ alkyl chain or a $NH_2$, NHY or NYY group where Y is a $C_1$ to $C_4$ alkyl chain.

2. The peptide compound according to claim 1, wherein said peptide of general formula (I) comprises at least one protective group protecting at least one functional group, said protective group selected from an acetylation of the amino-terminal end or an amidation or esterification of the carboxy-terminal end, or both.

3. The peptide compound according to claim 1, wherein said peptide is selected from the group consisting of (SEQ ID no. 1)  Ser-Pro-Leu-Gln-NH$_2$ (SEQ ID no. 2)  Thr-Ser-Pro-Leu-Gln (SEQ ID no. 3)  Ser-Ser-Pro-Leu-Gln-Leu-NH$_2$ (SEQ ID no. 4)  Ser-Ser-Pro-Leu-Gln-Ala-Asn-NH$_2$.

4. A cosmetic composition comprising;

a peptide compound of general formula (I) below:

$$R_1-X_1-X_2-Ser-Pro-Leu-Gln-X_3-X_4-R_2$$

wherein $X_1$ is a cysteine, a methionine or is equal to zero, $X_2$ is a serine, a threonine, or is equal to zero, $X_3$ is an alanine, a glycine, an isoleucine, a leucine, a proline, a valine or is equal to zero, $X_4$ is an asparagine, a glutamine, or is equal to zero, $R_1$ is the primary amine function of the N-terminal amino acid, either free or substituted by a protective group which can be selected from an acetyl group, a benzoyl group, a tosyl group or a benzyloxycarbonyl group, $R_2$ is the hydroxyl group of the carboxyl function of the C-terminal amino acid, either free or substituted by a protective group which can be selected from a $C_1$ to $C_{20}$ alkyl chain or a $NH_2$, NHY or NYY group where Y is a $C_1$ to $C_4$ alkyl chain, said sequence of general formula (I) being formed of 4 to 8 amino acid residues.

5. The cosmetic composition according to claim 4, wherein said peptide is in a form adapted for topical application and comprises cosmetically acceptable medium.

6. The composition according to claim 4, wherein said peptide compound is present in the composition at a concentration between approximately 0.0005 and 500 parts per million (ppm).

7. The composition according to claim 4, wherein said peptide is solubilized in one or more solvents selected from the group consisting of water, glycerol, ethanol, propylene glycol, butylene glycol, dipropylene glycol, ethoxylated or propoxylated diglycols, cyclic polyols, petroleum jelly, a vegetable oil, and combinations thereof.

8. A cosmetic treatment method for treating the cutaneous signs of aging or to protect the skin against the harmful effects caused by ultraviolet (UV) radiation, the method comprising:
topically applying, to skin or skin appendages to be treated, a composition comprising an effective quantity of a peptide compound of general formula (I) below:

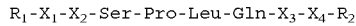

$$R_1-X_1-X_2-Ser-Pro-Leu-Gln-X_3-X_4-R_2$$

wherein
$X_1$ is a cysteine, a methionine or is equal to zero,
$X_2$ is a serine, a threonine, or is equal to zero,
$X_3$ is an alanine, a glycine, an isoleucine, a leucine, a proline, a valine or is equal to zero,
$X_4$ is an asparagine, a glutamine, or is equal to zero,
$R_1$ is the primary amine function of the N-terminal amino acid, either free or substituted by a protective group which can be selected from an acetyl group, a benzoyl group, a tosyl group or a benzyloxycarbonyl group,
$R_2$ is the hydroxyl group of the carboxyl function of the C-terminal amino acid, either free or substituted by a protective group which can be selected from a $C_1$ to $C_{20}$ alkyl chain or a $NH_2$, NHY or NYY group where Y is a $C_1$ to $C_4$ alkyl chain,
said sequence of general formula (I) being formed of 4 to 8 amino acid residues.

9. The cosmetic treatment method of claim 8, wherein topically applying includes applying the composition before going to sleep.

10. The composition of claim 6, wherein the peptide compound is present at a concentration between 0.01 and 5 parts per million (ppm).

11. The composition according to claim 4, wherein the peptide compound of general formula (I) comprises at least one protective group protecting at least one functional group, said protective group selected from an acetylation of the amino-terminal end or an amidation or esterification of the carboxy-terminal end, or both.

12. The composition of claim 4, wherein the peptide compound is selected from the group consisting of

| | |
|---|---|
| (SEQ ID no. 1) | Ser-Pro-Leu-Gln-NH$_2$ |
| (SEQ ID no. 2) | Thr-Ser-Pro-Leu-Gln |
| (SEQ ID no. 3) | Ser-Ser-Pro-Leu-Gln-Leu-NH$_2$ |
| (SEQ ID no. 4) | Ser-Ser-Pro-Leu-Gln-Ala-Asn-NH$_2$. |

13. The method of claim 8, wherein the peptide of general formula (I) comprises at least one protective group protecting at least one functional group, said protective group selected from an acetylation of the amino-terminal end or an amidation or esterification of the carboxy-terminal end, or both.

14. The method of claim 8, wherein the peptide compound is selected from the group consisting of

| | |
|---|---|
| (SEQ ID no. 1) | Ser-Pro-Leu-Gln-NH$_2$ |
| (SEQ ID no. 2) | Thr-Ser-Pro-Leu-Gln |
| (SEQ ID no. 3) | Ser-Ser-Pro-Leu-Gln-Leu-NH$_2$ |
| (SEQ ID no. 4) | Ser-Ser-Pro-Leu-Gln-Ala-Asn-NH$_2$. |

* * * * *